United States Patent [19]

Gilbert et al.

[11] Patent Number: 5,627,297
[45] Date of Patent: May 6, 1997

[54] PROCESS FOR CLEAVING THE BY-PRODUCTS OF THE DIRECT SYNTHESIS OF ALKYLCHLOROSILANES

[75] Inventors: Laurent Gilbert, Paris; Gilles Laroze, Genas, both of France

[73] Assignee: Rhone-Poulenc Chimie, Courbevoie, France

[21] Appl. No.: 628,179

[22] Filed: Apr. 4, 1996

[30] Foreign Application Priority Data

Apr. 10, 1995 [FR] France ................... 95 04486

[51] Int. Cl.⁶ .................................. C07F 7/08
[52] U.S. Cl. .......................... 556/467; 556/468
[58] Field of Search ..................... 556/467, 468

[56] References Cited

U.S. PATENT DOCUMENTS

| | | | |
|---|---|---|---|
| 5,175,329 | 12/1992 | Bokerman et al. | 556/467 |
| 5,288,892 | 2/1994 | Pachaly | 556/466 |
| 5,321,147 | 6/1994 | Chadwick et al. | 556/468 X |
| 5,430,168 | 7/1995 | Ferguson et al. | 556/467 |
| 5,502,230 | 3/1996 | Mautner et al. | 556/468 X |

FOREIGN PATENT DOCUMENTS 0574912  12/1993  European Pat. Off. .

OTHER PUBLICATIONS

Journal of Organometallic Chemistry, vol. 74, 1974, pp. 371–376 Calas et al.

*Primary Examiner*—Paul F. Shaver
*Attorney, Agent, or Firm*—Andrew M. Solomon

[57] ABSTRACT

The process for cleaving the heavy by-products derived from the synthesis of alkylchlorosilanes, in particular $C_1$ to $C_6$ alkylchlorosilanes, more particularly methylchlorosilanes, in particular for the cleavage of alkylchlorodisilanes, in particular methylchlorodisilanes having from one to five chlorine atoms, is carried out by treatment with hydrochloric acid in the presence of a catalytic system which comprises at least one metal phosphate, preferably associated with a basic impregnation compound.

The metal phosphate may in particular correspond to the formula:

$$M(XPO_4)_y$$

in which M represents a metal chosen from:
monovalent metals, in which case X is 2H and y=1
divalent metals, in which case X is H and y=1
trivalent metals, in which case X is absent and y=1
tetravalent metals, in which case X is: H and y=2
pentavalent metals, in which case X is 0 and y=1.

31 Claims, No Drawings

PROCESS FOR CLEAVING THE BY-PRODUCTS OF THE DIRECT SYNTHESIS OF ALKYLCHLOROSILANES

The present invention relates to a process for cleaving the heavy by-products derived from the synthesis of alkylchlorosilanes, in particular methylchlorosilanes, especially for cleaving alkylchlorodisilanes and in particular methylchlorodisilanes and, among these, especially those having from one to five chlorine atoms, by treatment with hydrochloric acid in the presence of a catalytic system.

Methylchlorosilanes are obtained by the action of methyl chloride on silicon metal (direct synthesis). Although this reaction is of very high performance, it co-produces many heavy by-products, namely silylmethylenes, polysilanes, disiloxanes, hydrocarbons and in particular methylchlorodisilanes which represent the major fraction (more than 80%). These by-products have no important industrial outlets and it is thus advantageous to seek to upgrade their value by cleaving the Si—Si bond. Some of these by-products may be upgraded by retrogradation into monosilanes by the HCl+amine reference process: this relates to disilanes having at least two chlorine atoms on at least one of the silicon atoms; they are qualified as being "cleavable". The others are noncleavable: $Me_2ClSi$-$SiClMe_2$ (symmetrical tetraethyldichlorodisilane), pentamethylchlorodisilane, silylmethylenes and polysilanes.

Many studies have already been performed on the cleavage of disilanes and, in particular, on the cleavage with hydrochloric acid in the presence of a catalytic system. Thus, various catalytic systems have already been described, such as the amines or tertiary amines described in patents FR-A-1,119,915 and FR-A-1,447,304 (HCl+amine reference process mentioned above). The catalytic system described in these patents makes it possible efficiently to convert tetrachlorodimethyldisilane and trichlorotrimethyldisilane and certain tetramethyldichlorodisilanes, but has the drawback of not being able to cleave all disilanes and, in particular, does not convert symmetrical tetramethyldichlorodisilane.

Organometallic complexes of palladium make it possible to overcome this problem by means of the use of harsher reaction conditions. Furthermore, the use of such a catalytic system is limited industrially by the difficulty in recycling a homogeneous catalyst. Under the conditions described (H. Matsumoto et al., Bulletin of the Chemical Society of Japan, Vol. 51 (6), 1913–1914, 1978) the flow rates treated remain low and the material balances are poor.

In this respect, patent U.S. Pat. No. 3,772,347 proposes to treat with a halide RCl in the presence of transition metal complexes, for example a phosphine-palladium complex, optionally supported on charcoal or silica gel, leading to the production of about 25% by weight of hydrogenosilanes. This process describes the cleavage of tetramethyldichlorodisilane with a reaction time of 86 hours.

Similarly, patent U.S. Pat. No. 5,210,255 proposes to use, in heterogeneous catalysis, a metal from subgroup VIII of the Periodic Table (IUPAC standard), such as platinum, palladium, rhodium or ruthenium, in particular in the form of a catalyst supported, for example, on active charcoal. Palladium is the preferred metal. The object would appear to be to obtain unhydrogenated methylchlorosilanes. A comparison is made between palladium-on-charcoal and tetrakis(triphenylphosphine)palladium. The first would appear to lead to good yields of retrogradation of the disilanes into unhydrogenated monosilanes, whereas the second leads to the production of a considerable level of hydrogenosilanes $MeHSiCl_2$ and $Me_2HSiCl$, but in a poor yield. The cleavage kinetics are slow: contact time of several hours.

The thermal cleavage in the vapour phase at 500° C. described in patents U.S. Pat. No. 5,292,912, U.S. Pat. No. 5,292,902, U.S. Pat. No. 5,321,147 and U.S. Pat. No. 5,326,896 also makes it possible, in the presence of hydrochloric acid, chlorine and/or hydrogen gas, to cleave all of the disilanes on various catalysts such as activated charcoal, metal oxides, zeolites or supported metals. At this temperature, the reactions are mainly thermal and little hydrogenosilane is obtained. Moreover, it is well known that the catalysts used are modified by reaction of the chlorosilanes, which will modify their catalytic properties.

There is thus still a need for a process which makes it possible to cleave the by-products of the direct synthesis and, in particular, symmetrical tetramethyldichlorodisilane, under industrially advantageous conditions.

The object of the present invention is thus to overcome the drawbacks of the prior art by providing a process which makes it possible to cleave, under mild and rapid conditions, the by-products of the direct synthesis and which makes it generally possible to cleave all of the disilanes, in particular methylchlorodisilanes having from one to five chlorine atoms, and most particularly symmetrical tetramethyl dichlorodisilane, as well as pentamethylchlorodisilane, under industrially acceptable conditions.

Another object of the invention is also to allow the cleavage of other heavy products, in particular of the type:
$(Me)_xCl_ySiCH_2Si(Me)_zCl_t$, or
$(Me)_xCl_ySiSi(Me)_wCl_u[Si(Me)_zCl_t]_n$ with n greater than or equal to 1, in particular between 1 and 8
where:
x=0 to 3, y=0 to 3, with x+y=3;
z=0 to 3, t=0 to 3, with z+t=3;
w=0 to 2, u=0 to 2, with w+u=2;
and at least y or t or u is at least equal to 1.

A further object of the invention is to provide such a process which leads to the production of an appreciable amount of industrially advantageous hydrogenosilanes.

The subject of the present invention is thus a process for cleaving the heavy by-products derived from the direct synthesis of alkylchlorosilanes, in particular $C_1$ to $C_6$ alkylchlorosilanes, especially for the cleavage of alkylchlorodisilanes, by treatment with hydrochloric acid in the presence of a catalytic system, characterized in that the catalytic system comprises at least one metal phosphate.

The present invention is preferably applied to the cleavage of the heavy by-products derived from the synthesis of methylchlorosilanes and most particularly to the cleavage of methylchlorodisilanes having from one to five chlorine atoms.

Preferably, the metal phosphate comprises a compound of basic impregnation, chosen in particular from the group of alkaline-earth metals, that of alkali metals, and mixtures thereof (by definition intra- and/or inter-group mixtures), preferably associated with a counter-anion to ensure the electrical neutrality. The initial counter-anion(s), that is to say the counter-anion(s) before thermal treatment, may advantageously be chosen from nitrate, sulphate, chloride, fluoride, hydrogen phosphate, phosphate, dihydrogen phosphate, hydrogen sulphate, oxalate, acetate, benzoate, etc. anions. The anions may be a single species or may consist of a mixture of species; for reasons of simplicity, it is preferred to have only a single species or family of species. The content of impregnation compound (or doping agent) in the catalyst is preferably such that the weight percentage of basic impregnation compound, expressed in particular as alkali metal and/or alkaline-earth metal element, relative to the dry metal phosphate is between 0 and 25%, advantageously between 3 and 15%.

Preferably, the metal phosphate comprises a metal chosen from the group consisting of monovalent, divalent and trivalent metals:, including rare earth metals, tetravalent and pentavalent metals.

Preferably also, the metal phosphate corresponds to the formula:

$$M(XPO_4)_y$$

in which M represents a metal chosen from:
monovalent metals, in which case X is 2H and y =1
divalent metals, in which case X is H and y=1
trivalent metals, in particular such as Al, B, Fe, Ga and rare earth metals (lanthanides having an atomic number from 57 to 71, including lanthanum, in particular lanthanides as mentioned above, as well as yttrium and scandium), in which case X is absent and y=1
tetravalent metals, in particular such as Zr, Ti, etc., in which case X is H and y=2
pentavalent metals, in particular such as Nb, Ta, etc., in which case X is 0 and y=1.

In a particularly preferred embodiment, the invention provides for the use of a metal phosphate based on the use of trivalent rare earth metal. The metal phosphate then advantageously corresponds to the formula:

$$MPO_4$$

in which:
M represents:
a trivalent rare earth metal $M_3$, or
a mixture of at least one trivalent rare earth metal $M_3$ and at least one element chosen from the group consisting of alkali metals $M_1$ and alkaline-earth metals $M_2$ with the relationship:

$$M=aM_1+bM_2+cM_3 \text{ and } a+2b+3c=3$$

a is a coefficient between 0 and 3, advantageously between 0.01 and 0.5, preferably between 0.05 and 0.2,
b is a coefficient between 0 and ½, advantageously between 0 and ⅓ or alternatively 1±0.1, and
c is a coefficient between 0 and 1, advantageously greater than or equal to ⅓, preferably to ½.

It is thus preferred for the metal phosphate additionally to comprise an impregnation compound, such that its formula consequently becomes:

$$MPO_4(Im)_p$$

in which:
Im corresponds to a basic impregnation compound consisting of a metal chosen from the group consisting of alkaline-earth metals, alkali metals and mixtures thereof, preferably associated with a counter-anion in order to ensure the electrical neutrality, and
p is less than 0.5, in particular between 0.04 and 0.25.
Preferably,
$M_1$ is chosen from the group of elements from column 1A, preferably alkali metals such as lithium, sodium, potassium, rubidium or caesium, and mixtures thereof,
$M_2$ is chosen from the group of elements from column 2A, preferably alkaline-earth metals such as beryllium, magnesium, calcium, strontium or barium, and mixtures thereof, $M_3$ is chosen from the group of trivalent rare-earth metals chosen from lanthanides, yttrium and scandium, and mixtures thereof, the lanthanides preferably being lanthanum, cerium, praseodymium, neodymium, samarium, europium, gadolinium, terbium, dysprosium, holmium, erbium, thulium, ytterbium and lutetium.

By definition, reference is made to the classification of the elements published in the Bulletin de la Société Chimique de France, No. 1, 1966.

In general, M preferably consists of at most three elements, for reasons of convenience. For the same reasons, it may be economically advantageous to use commercial mixtures of rare earth metals in whatever forms they are in, as long as they lead readily to the compounds according to the invention.

The metal phosphates according to the invention may be prepared by impregnation of the phosphate, in particular of the compound of formula $MPO_4$, with a solution or a suspension of $Im_p$ in a volatile solvent, preferably such as water.

The results are proportionately better the more soluble $Im_p$ is and the more freshly manufactured the phosphate, in particular $MPO_4$, is.

Thus, an advantageous process for the preparation of the phosphates of formula $MPO_4$ (Im)p consists:
a) in synthesizing the compound $MPO_4$, followed, preferably without separating $MPO_4$ from the reaction medium, by
b) introducing the impregnating agent $Im_p$ into the reaction medium,
c) separating the possible residual liquid from the reaction solid,
d) drying and optionally calcinating.

If reference is made to the general techniques for the preparation of phosphates (such as those described in particular in "Pascal P., Nouveau Traité de Chimie Minérale [New Treatise on Inorganic Chemistry]" Volume X (1956), pages 821–823 and in "Gmelins, Handbuch der Anorganischen Chemie [Handbook of Inorganic Chemistry]" (8th Edition) Volume 16 (C), pages 202–206 (1965), two main routes of access to phosphates may be distinguished. On the one hand, the precipitation of a soluble metal salt (chloride, nitrate) with ammonium hydrogen phosphate or phosphoric acid and finishing treatment with aqueous ammonia, optionally followed by additional neutralization. On the other hand, reaction of the metal oxide with phosphoric acid under hot conditions. In both cases a finishing treatment with an alkaline hydroxide may be envisaged.

The phosphates of the said metals may also be prepared by grogging (solid-solid reaction) of their salts with phosphorus salts, followed by calcination.

The product is then dried according to the standard techniques known to those skilled in the art. This is advantageously carried out between 50° C. and 200° C., for a period ranging preferably from 2 to 8 hours, under normal atmosphere or under reduced pressure or by freeze-drying. The dried product may then be calcined at a temperature of between 200° C. and 1000° C., preferably between 400° C. and 700° C., for a period ranging from 1 to 15 hours, preferably 3 to 6 hours.

For the preparation of the doped/impregnated phosphates according to the invention, reference may also be made to patent applications EP-A-0,440,555 and EP-A-0,599,688 which are incorporated here by way of reference.

The cleavage proceeds may be carried out in the vapour phase (HCl gas and vaporized products to be cleaved) or in a gas-liquid-solid three-phase system (HCl gas, products to be cleaved in solution), the catalyst in both cases preferably being in solid form. It may be carried out either continuously or discontinuously (batch) with continuous distillation or accumulation of the reaction products.

The catalyst used, in the case of the vapour phase process, may be arranged in a fixed bed or may be used in a fluidized bed, in particular as a mixture with inert materials, so as to increase the contact surface, or, in the case of the three-phase system process, may be used in suspension (slurry).

The cleavage process is generally carried out at a temperature of 100° C. to 500° C. In the case of disilanes comprising two or more chloride atoms per silicon atom, the temperature may be between 100° C. and 300° C. For the other disilanes or heavy products, the reaction temperature is advantageously between 300°, preferably 350° C., and 500° C. When a mixture of all of the heavy products is used, reactions of cleavage of heavy products or of products not comprising two chlorine atoms per silicon atom may also be observed, even at a lower temperature, for example 200° C. During an implementation in the vapour phase, the contact time, defined as the ratio between the volume of the catalyst and the total flow rate of gas (disilane+hydrochloric acid+ carrier gas) at the chosen temperature commonly ranges from 0.01 second to 50 seconds and usually from 0.1 second to 10 seconds.

The pressure is not critical. It is generally from atmospheric pressure to 10 MPa (100 bar) and preferably from atmospheric pressure to 1.5 MPa (15 bar).

The molar ratio between the hydrochloric acid and all of the disilanes may be between 0.1 and 100, preferably between 0.5 and 10. An inert carrier gas whose partial pressure represents between 0 and 10% of the entire gas flow may also be used. The inert carrier gas may consist of a gas or a mixture of gases which is inert under the reaction conditions, for example such as argon, nitrogen, etc.

During an implementation in suspension (slurry), the catalyst may be suspended in a mixture of the disilanes and other heavy products derived from the direct synthesis, but also in an inert organic solvent whose boiling point is high, between 80° C. and 300° C. The organic solvent is chosen for its capacity to solubilize the disilanes. Inert solvents which may be mentioned are cyclic carboxamides, aliphatic or aromatic nitriles, ethers, etc. The monosilanes produced may be distilled continuously as they are formed or may be recovered at the end of the reaction.

The implementation in vapour phase and in a fixed bed is preferred and leads remarkably to a high-performance cleavage of the symmetrical tetramethyldichlorodisilane with a contact time which is advantageously very short, of the order of a few seconds, for example of about 2 seconds or even less. This implementation also leads, quite remarkably, to an extremely high-performance cleavage of the other methylchlorodisilanes. Thus, degrees of conversion (of cleavage) of 99 to 100% have been achieved for the treatment of trimethyltrichlorodisilane+dimethyltetrachlorodisilane mixtures, with very short contact times, of 3 and 0.6 seconds respectively. Similar degrees of conversion have been obtained with a mixture of industrial type comprising the three abovementioned disilanes. The very short reaction times represent a great advantage in industrial terms, in particular as regards the reactor which may thus be of very small size while at the same time treating a considerable volume.

The invention has another remarkable advantage inasmuch as the high-performance cleavage of the symmetrical tetramethyldichlorodisilane is accompanied by the production of hydrogenosilane $Me_2HSiCl$, which is currently the compound with the greatest commercial value.

For the implementation in suspension, the catalyst is preferably impregnated. The reaction time is of the order of a few minutes to a few hours, especially between 5 min and 5 h, in particular between 30 min and 2 h.

The process according to the invention also has the advantage of allowing the production of hydrogenosilanes $Me_2HSiCl$ and $MeHSiCl_2$.

The examples which follow illustrate the invention without, however, limiting it.

EXAMPLES

Preparation of lanthanum phosphate:

Example 1

106 g of $H_3PO_4$ (at a concentration of 85%, sold by the company Prolabo), i.e. 0.92 mol in 800 ml of deionized water are introduced into a reactor.

The mixture is stirred at 500–700 revolutions/minute.

299 g of $La_2(CO_3)_3.12H_2O$, i.e. 0.8 mol of lanthanum, in 736 ml of water are introduced slowly and with vigorous stirring, under cold conditions.

The reaction medium is then heated at 80° C. for 2 hours 30 minutes.

The mixture is allowed to cool to room temperature, without stirring, over half an hour and the cooling is completed in a bath of cold water.

The suspension is filtered through a No. 3 sinter funnel until the mother liquors are exhausted.

The product is then redispersed in two liters of water, with vigorous stirring, and is left in suspension for half an hour, while stirring is continued.

The suspension is filtered through a No. 3 sinter funnel until the mother liquors are exhausted. The product is redispersed in 900 ml of deionized water and neutralized with aqueous ammonia solution to a pH equal to 9.

The product is filtered, washed with water and centrifuged before being dried at 110° C.

Some of the product thus obtained is then calcined for 4 hours at 400° C.

Example 2

The product prepared according to Example 1, dried at 110° C., is calcined for 4 hours at 700° C.

Preparation of lanthanum phosphate doped with an alkali metal salt:

Example 3

7.8 ml of 6M CsOH solution are taken, to which are added 23.5 ml of 1M $H_3PO_4$ solution. The amount of water required to complete to 50 ml is then added. 50 g of product prepared in Example 1 are taken and placed in a 200 ml beaker. 20 ml of the impregnation solution prepared above are introduced dropwise while homogenizing thoroughly. The product is left to stand for one hour. It is dried overnight at 110° C. and is calcined for 2 hours at 500° C.

Caesium content of the solids=5%.

Example 4

The process is performed as in Example 2 using an impregnation solution prepared from 15.7 ml of 6M CsOH solution and 23.5 ml of 2M $H_3PO_4$ solution.

Caesium content of the solids=10%.

Example 5

The process is performed as in Example 2 using an impregnation solution prepared from 16.3 ml of 6 M CsOH solution and 24 ml of 4M $H_3PO_4$ solution.

Caesium content of the solids=13%.

Example 6

The process is performed as in Example 2 using an impregnation solution prepared from 4.7 ml of 6M KOH solution and 14.1 ml of 1M $H_3PO_4$ solution.

Potassium content of the solids=0.88%.

Example 7

182.4 g of $H_3PO_4$ (at a concentration of 85%, sold by the company Prolabo), i.e. 1.6 mol, in 640 ml of deionized water are introduced into a reactor.

The reaction medium is heated to 85° C. and, when the temperature is reached, 260.8 g of $La_2O_3$ (i.e. 0.8 mol of lanthanum) are introduced steadily (14 g every 5 minutes). The reaction mixture is heated at 85° C. for 1 hour and is then cooled to room temperature with stirring.

1M CsOH solution is then added, with vigorous stirring, until a solution of pH 9 is obtained.

The product is recovered by centrifugation (3,600 revolutions/minute) and then redispersed in 400 ml of deionized water. The product thus washed is recovered by centrifugation. This washing operation is repeated four times according to the same procedure. The product thus washed is dried at 110° C. and then calcined for 4 hours at 500° C.

Example 8

Preparation of zirconium hydrogen phosphate:

93 ml of 10.33M $H_3PO_4$ are introduced into a reactor fitted with a condenser and a paddle stirrer. The $H_3PO_4$ is then brought to the boil (stirring at 300 rev/minute) using an oil bath on a heating plate, in which the temperature is controlled by means of a contact thermometer. At this point, 0.064 mol of zirconium sulphate is introduced. The pasty product becomes pale yellow (over ½ h). The temperature is then lowered to 80° C. and the mixture is left for 48 hours. After cooling, the product obtained is recovered and is centrifuged for 25 minutes. The product is washed a first time with hot water (80° C.) and then with cold water until the washing waters have a pH of 4. The product is dried under vacuum for 40 hours.

Example 9

Preparation of calcium hydrogen phosphate:

106.6 g of $Ca(NO_3)_2$ are dissolved in 300 ml of $H_2O$ (pH of the solution about 7) in a beaker. A solution of $(NH_4)_2HPO_4$ in deionized $H_2O$ (m=145.2 g in 300 ml of $H_2O$) is then introduced at a flow rate of 1.2 liters/hour. The product precipitates out. The introduction is completed and a further 50 ml of $H_2O$ are introduced (rinsing of the pump tubes). The mixture is then left stirring at room temperature for 4 hours. 413.7 g of suspension are taken. Centrifugation is then carried out for 20 minutes (pH of the mother liquors=6.7). Washing is carried out with 500 ml of $H_2O$, stirring for 20 minutes. The product is centrifuged and washed (pH of the washing waters=7.8). The product is dried and then calcined for 3 hours at 500° C.

A—Examples 10 to 13 illustrate an implementation in a three-phase system, in a reactor working batchwise, the catalyst being maintained in suspension (slurry).

General procedure

After flushing the apparatus with nitrogen for one hour, the disilane and the catalyst are introduced into a three-necked reactor fitted with a vertical condenser, a gas inlet and means for measuring the temperature, then heating is begun, still under a stream of nitrogen.

When reflux is achieved (145°–150° C.), the input of nitrogen is cut off and hydrochloric acid is supplied. When the reaction has stopped, the HCl input is cut off and the apparatus is then flushed with nitrogen.

The reaction products are analysed by gas chromatography (GC).

The following are thus calculated for each test:

the degree of conversion (DC):% of disilane converted relative to the disilane introduced the selectivities for monosilanes by normalization to 100.

Examples 10 to 13

Table 1: Degree of conversion
Table 2: Monosilanes formed (selectivity by normalization to 100)

TABLE 1

| Example | Catalyst | Disilane | Percentage by weight of catalyst relative to the disilane | Duration (hours) | HCl (equivalents) | Degree of conversion (%) |
|---|---|---|---|---|---|---|
| 10 | $Zr(HPO_4)_2$ prepared according to Example 8 | $Me_2ClSi$—$SiCl_2Me$ 27% $MeCl_2Si$—$SiCl_2Me$ 61% | 4 | 3.5 | 12 | Overall: 16 $Me_2ClSi$—$SiCl_2Me$: 19 $MeCl_2Si$—$SiCl_2Me$: 14 |
| 11 | $LaPO_4.Cs_2HPO_4$ 13% w/w Cs prepared according to Example 5 | $Me_2ClSi$—$SiCl_2Me$ 27% $MeCl_2Si$—$SiCl_2Me$ 61% | 4 | 3.5 | 12 | Overall: 18 $Me_2ClSi$—$SiCl_2Me$: 24 $MeCl_2Si$—$SiCl_2Me$: 15 |
| 12 | $LaPO_4.Cs$ prepared according to Example 7 | $Me_2ClSi$—$SiCl_2Me$ 27% $MeCl_2Si$—$SiCl_2Me$ 61% | 13 | 3.5 | 12 | Overall: 19 $Me_2ClSi$—$SiCl_2Me$: 26 $MeCl_2Si$—$SiCl_2Me$: 17 |
| 13 | $LaPO_4.K_2HPO_4$ 0.88% w/w K prepared according to Example 8 | $Me_2ClSi$—$SiCl_2Me$ 27% $MeCl_2Si$—$SiCl_2Me$ 61% | 4 | 3.5 | 12 | Overall: 0.5 |

TABLE 2

| Example | Catalyst | DC (%) | $Me_2SiCl_2$ | $MeSiCl_3$ | $Me_3SiCl$ | $MeHSiCl_2$ | Others |
|---|---|---|---|---|---|---|---|
| 10 | $Zr(HPO_4)_2$ | 16 | 27 | 35 | 1 | 8 | 29 |
| 11 | $LaPO_4.Cs_2HPO_4$ 13% w/w Cs | 18 | 35 | 34 | 3 | 3 | 25 |
| 12 | $LaPO_4.Cs$ | 19 | 40 | 40 | 3 | 2 | 15 |
| 13 | $LaPO_4.K_2HPO_4$ 0.88% w/w K | 0.5 | 29 | 31 | — | — | 40 |

B—Examples 14 to 26 below illustrate an implementation in the vapour phase in a fixed bed.

General procedure:

The catalysts will be tested according to the following procedure, except where otherwise mentioned:

5 cm³ of quartz, the catalyst and then 5 cm³ of quartz are successively loaded into a reactor arranged vertically (quartz tube 15 cm in length and 2 cm in diameter). The catalyst is conditioned at the temperature chosen for the reaction, by passage of a stream of nitrogen for two hours (2 liters/hour under standard temperature and pressure conditions).

The chlorodisilanes are then injected by means of a syringe pump. The flow rate is adjusted to obtain the contact time chosen for each experiment. After establishing the conditions for about 15 minutes, the test generally lasts 1 hour. The products leaving the reactor are trapped in a receiver cooled with a bath of water maintained at 0° C. The reaction products are analysed by gas chromatography (GC).

The following are thus calculated for each test:

the degree of conversion (DC):% of disilane converted relative to the disilane introduced, the selectivities for monosilanes by normalization to 100.

Examples 14 to 20 tests of cleavage of $Me_2ClSi-SiClMe_2$ (85% w/w):
Table 3: degree of conversion Table 4: monosilanes formed (selectivity by normalization to 100)

Examples 21 to 25 tests of cleavage of $Me_2ClSi-SiCl_2Me$ (27%)+$MeCl_2Si-SiCl_2Me$ (61%)

Table 5: degree of conversion

Table 6: monosilanes formed (selectivity by normalization to 100)

Example 26 test of cleavage of a mixture of industrial type: $Me_2ClSi-SiClMe_2$ (25% w/w)+$Me_2ClSi-SiCl_2Me$ (22% w/w)+$MeCl_2Si-SiCl_2Me$ (49% w/w)

Table 7: degree of conversion

Table 8: monosilanes formed (selectivity by normalization to 100).

TABLE 3

| Example | Catalyst | Temperature (°C.) | HCl (equivalents) | Contact time (seconds) | Degree of conversion (%) |
|---|---|---|---|---|---|
| 14 | Quartz porosity 0 | 400 | 5 | — | 0 |
| 15 | $LaPO_4$ prepared according to Example 2 | 400 | 5 | 2 | 23 |
| 16 | $LaPO_4.Cs_2HPO_4$ (5% w/w Cs) prepared according to Example 3 | 400 | 5 | 2 | 33 |
| 17 | $LaPO_4.Cs_2HPO_4$ (10% w/w Cs) prepared according to Example 4 | 400 | 5 | 2 | 54 |
| 18 | $LaPO_4.Cs_2HPO_4$ (13% w/w Cs) prepared according to Example 5 | 435 | 21 | 0.5 | 12 |
| 19 | $LaPO_4.K_2HPO_4$ (0.88% w/w K) prepared according to Example 6 | 400 | 5 | 2 | 15 |
| 20 | $Zr(HPO_4)_2$ prepared according to Example 8 | 400 | 5 | 2 | 14 |

TABLE 4

| Example | Catalyst | DC (%) | $Me_2SiCl_2$ | $MeSiCl_3$ | $Me_3SiCl$ | $MeHSiCl_2$ | $Me_2HSiCl$ | Others |
|---|---|---|---|---|---|---|---|---|
| 15 | $LaPO_4$ | 23 | 70 | 18 | — | 2 | 2 | 8 |
| 16 | $LaPO_4.Cs_2HPO_4$ (5% w/w Cs) | 33 | 81 | 4 | — | — | 15 | 0 |
| 17 | $LaPO_4.Cs_2HPO_4$ (10% w/w Cs) | 54 | 89 | — | — | — | 6 | 5 |

TABLE 4-continued

| Example | Catalyst | DC (%) | $Me_2SiCl_2$ | $MeSiCl_3$ | $Me_3SiCl$ | $MeHSiCl_2$ | $Me_2HSiCl$ | Others |
|---|---|---|---|---|---|---|---|---|
| 18 | $LaPO_4.Cs_2HPO_4$ (13% w/w Cs) | 12 | 76 | — | — | — | 16 | 8 |
| 19 | $LaPO_4.K_2HPO_4$ (0.88% w/w Cs) | 15 | 78 | 10 | — | — | 11 | 1 |
| 20 | $Zr(HPO_4)_2$ | 14 | 75 | 4 | 1 | 1 | 5 | 14 |

Tests of cleavage of $Me_2ClSi—SiCl_2Me$ (27%)+$MeCl_2Si—SiCl_2Me$ (61%)

TABLE 5

| Example | Catalyst | Temperature (°C.) | HCl (equivalents) | Contact time (seconds) | Degree of conversion (%) |
|---|---|---|---|---|---|
| 21 | Quartz porosity 0 | 200 | 5 | — | 0 |
| 22 | $LaPO_4$ prepared according to Example 1 | 200 | 5 | 3 | Overall: 2 |
| 23 | $LaPO_4$ prepared according to Example 2 | 200 | 5 | 3 | Overall: 3 |
| 24 | $LaPO_4.Cs_2HPO_4$ (5% w/w Cs) prepared according to Example 3 | 200 | 5 | 3 | Overall: 100 |
| 25 | $LaPO_4.Cs_2HPO_4$ (5% w/w Cs) prepared according to Example 3 | 200 | 5 | 0.6 | $Me_2ClSi—SiCl_2Me$: 99 $MeCl_2Si—SiCl_2Me$: 99 |

TABLE 6

| Example | Catalyst | DC (%) | $Me_2SiCl_2$ | $MeSiCl_3$ | $Me_3SiCl$ | $MeHSiCl_2$ | $Me_2HSiCl$ | Others |
|---|---|---|---|---|---|---|---|---|
| 22 | $LaPO_4$ | 2 | 24 | 45 | — | 26 | — | 5 |
| 23 | $LaPO_4$ | 3 | 24 | 46 | — | 25 | — | 5 |
| 24 | $LaPO_4.Cs_2HPO_4$ (5% w/w Cs) | 100 | 17 | 60 | 1 | 22 | — | 0 |
| 25 | $LaPO_4.Cs_2HPO_4$ (5% w/w Cs) | 99 | 17 | 43 | 1 | 39 | — | 0 |

Tests of cleavage of $ME_2ClSi—SiClMe_2$ (25% w/w)+$Me_2ClSi—SiCl_2Me$ (22% w/w)+$MeCl_2Si—SiCl_2Me$ (49% w/w)

TABLE 7

| Example | Catalyst | Temperature (°C.) | HCl (equivalents) | Contact time (seconds) | Degree of conversion (%) |
|---|---|---|---|---|---|
| 26 | $LaPO_4.Cs_2HPO_4$ (5% w/w Cs) prepared according to Example 3 | 200 | 5 | 3 | $Me_2ClSi—SiClMe_2$: 5 $Me_2ClSi—SiCl_2Me$: 95 $MeCl_2Si—SiCl_2Me$: 100 |

TABLE 8

| Example | Catalyst | $Me_2SiCl_2$ | $MeSiCl_3$ | $Me_3SiCl$ | $MeHSiCl_2$ | $Me_2HSiCl$ | Others |
|---|---|---|---|---|---|---|---|
| 34 | $LaPO_4.Cs_2HPO_4$ (5% w/w Cs) | 20 | 61 | 1 | 18 | — | 0 |

What is claimed is:

1. A process for cleaving heavy by-products derived from the synthesis of alkylchlorosilanes, by treatment with hydrochloric acid in the presence of a catalytic system, wherein the catalytic system comprises at least one metal phosphate.

2. A process according to claim 1 wherein the alkylchlorosilanes are $C_1$ to $C_6$ alkylchlorosilanes.

3. A process according to claim 2 wherein the $C_1$ to $C_6$ alkylchlorosilanes are methylchlorosilanes.

4. A process according to claim 1 wherein the heavy by-products are alkylchlorodisilanes.

5. A process according to claim 4 wherein the alkylchlorodisilanes are methylchlorodisilanes having one to five chlorine atoms.

6. A process according to claim 1 wherein the metal phosphate further comprises a basic impregnation compound.

7. A process according to claim 6 wherein the basic impregnation compound is selecting from the group consisting of alkaline-earth metals, alkali metals, and mixtures thereof.

8. A process according to claim 7 wherein the basic impregnation compound is further associated with a counter-anion.

9. A process according to claim 6 wherein the weight percentage of basic impregnation compound relative to the metal phosphate is between 0 and 25%.

10. A process according to claim 9 wherein the weight percentage of basic impregnation compound is between 3 and 15%.

11. A process according to claim 1 wherein the metal phosphate comprises a metal chosen from the group consisting of monovalent, divalent, trivalent, tetravalent and pentavalent metals.

12. A process according to claim 11 wherein the metal is selected from the group consisting of rare earth metals.

13. A process according to claim 11 wherein the metal phosphate corresponds to the formula:

$$M(XPO_4)_y$$

in which M represents a metal selected from the group consisting of:

monovalent metals, in which case X is 2H and y=1
divalent metals, in which case X is H and y=1
trivalent metals, in which case X is absent and y=1
tetravalent metals, in which case X is H and y=2, and
pentavalent metals, in which case X is 0 and y=1.

14. A process according to claim 13 wherein the metal phosphate corresponds to the formula:

$$MPO_4$$

in which:

M represents:
a trivalent rare earth metal $M_3$, or
a mixture of at least one trivalent rare earth metal $M_3$ and at least one element selected from the group consisting of alkali metals $M_1$ and alkaline-earth metals $M_2$ with the relationship:

$$M=aM_1+bM_2+cM_3 \text{ and } a+2b+3c=3$$

a is a coefficient between 0 and 3
b is a coefficient between 0 and 3/2, and
c is a coefficient between 0 and 1.

15. A process according to claim 14 wherein the coefficient a is between 0.01 and 0.5.

16. A process according to claim 14 wherein the coefficient b is between 0 and 1/3.

17. A process according to claim 14 wherein the coefficient c is greater than 1/3.

18. A process according to claim 14 wherein a is between 0.05 and 0.2 or b is 1±0.1 or c is greater than or equal to ½.

19. A process according to claim 14 wherein the metal phosphate further comprises an impregnation compound, such that its formula consequently becomes:

$$MPO_4(Im)_p$$

in which:

Im corresponds to a basic impregnation compound comprising a metal selected from the group consisting of alkaline-earth metals, alkali metals and mixtures thereof, and p is less than 0.5.

20. A process according to claim 18 wherein $I_m$ is further associated with a counter-ion.

21. A process according to claim 18 wherein p is between 0.04 and 0.25.

22. A process according to claim 14 wherein
$M_1$ is selected from the group consisting of lithium, sodium, potassium, rubidium or cesium, and mixtures thereof,
$M_2$ is selected from the group consisting of beryllium, magnesium, calcium, strontium or barium, and mixtures thereof, and
$M_3$ is selected from the group consisting of lanthanides, yttrium and scandium, and mixtures thereof.

23. A process according to claim 1 wherein the treatment is carried out at a temperature of between 100° and 500° C.

24. A process according to claim 23 wherein the temperature is between 350° and 500° C.

25. A process according to claim 23 wherein the treatment is carried out at a temperature of between 100° and 300° C. for the cleavage of disilanes having two or more chlorine atoms per silicon atom.

26. A process according to claim 1 wherein the treatment is carried out in the vapor phase, with a solid catalyst in a fixed or fluidized bed.

27. A process according to claim 26 wherein the time of treatment is between 0.01 and 50 seconds.

28. A process according to claim 27 wherein the time of treatment is between 0.01 and 10 seconds.

29. A process according to claim 1 wherein the treatment is carried out in a gas-liquid-solid three-phase system with a solid catalyst in suspension.

30. A process according to claim 29 wherein the time of treatment is between 5 min and 5 hours.

31. A process according to claim 30 wherein the time of treatment is between 30 min and 2 hours.

* * * * *